United States Patent
Aresta et al.

(10) Patent No.: US 11,406,968 B2
(45) Date of Patent: Aug. 9, 2022

(54) MIXED OXIDES FOR THE OXIDATIVE CLEAVAGE OF LIPIDS USING OXYGEN TO AFFORD MONO- AND DI-CARBOXYLIC ACIDS

(71) Applicants: CATALISI INNOVATIVA PER IL RICICLO DEL CARBONIO E BIOPOLIMERI SRL, Bari (IT); NOVAMONT S.P.A., Novara (IT)

(72) Inventors: Michele Aresta, Bari (IT); Angela Dibenedetto, Altamura (IT); Daniele Cornacchia, Bari (IT)

(73) Assignees: CATALISI INNOVATIVA PER IL RICICLO DEL CARBONIO E BIOPOLIMERI SRL, Bari (IT); NOVAMONT S.P.A., Novara (IT)

( * ) Notice: Subject to any disclaimer, the term of this patent is extended or adjusted under 35 U.S.C. 154(b) by 891 days.

(21) Appl. No.: 16/303,567

(22) PCT Filed: May 24, 2017

(86) PCT No.: PCT/EP2017/062616
§ 371 (c)(1),
(2) Date: Nov. 20, 2018

(87) PCT Pub. No.: WO2017/202955
PCT Pub. Date: Nov. 30, 2017

(65) Prior Publication Data
US 2021/0220804 A1 Jul. 22, 2021

(30) Foreign Application Priority Data
May 24, 2016 (IT) .......... 102016000053407

(51) Int. Cl.
*B01J 23/847* (2006.01)
*B01J 23/00* (2006.01)
*B01J 23/648* (2006.01)
*B01J 37/00* (2006.01)
*B01J 37/08* (2006.01)
(Continued)

(52) U.S. Cl.
CPC ......... *B01J 23/8474* (2013.01); *B01J 23/002* (2013.01); *B01J 23/6484* (2013.01); *B01J 37/0036* (2013.01); *B01J 37/086* (2013.01); *C07C 51/25* (2013.01); *C07C 67/303* (2013.01); *C11C 3/006* (2013.01)

(58) Field of Classification Search
CPC .. B01J 23/8474; B01J 23/002; B01J 23/6484; B01J 37/0036; B01J 37/086; C07C 51/25; C07C 67/303; C11C 3/006
See application file for complete search history.

(56) References Cited

FOREIGN PATENT DOCUMENTS

| DE | 102010002603 A | 9/2011 |
| WO | WO 2007/039481 A1 | 4/2007 |
| WO | WO 2013/079849 A1 | 6/2013 |

OTHER PUBLICATIONS

International Search Report and Written Opinion issued in International Patent Application No. PCT/EP2017/062616 dated Aug. 8, 2017.

(Continued)

*Primary Examiner* — Deborah D Carr
(74) *Attorney, Agent, or Firm* — Arent Fox Schiff LLP

(57) ABSTRACT

This invention relates to the synthesis of new catalysts based on earth crust abundant mixed oxides that can produce cleavage of fatty acids (FA), FA methyl esters, or even lipids in a single step using oxygen as oxidant in solventless conditions.

11 Claims, 2 Drawing Sheets

Figure 1:
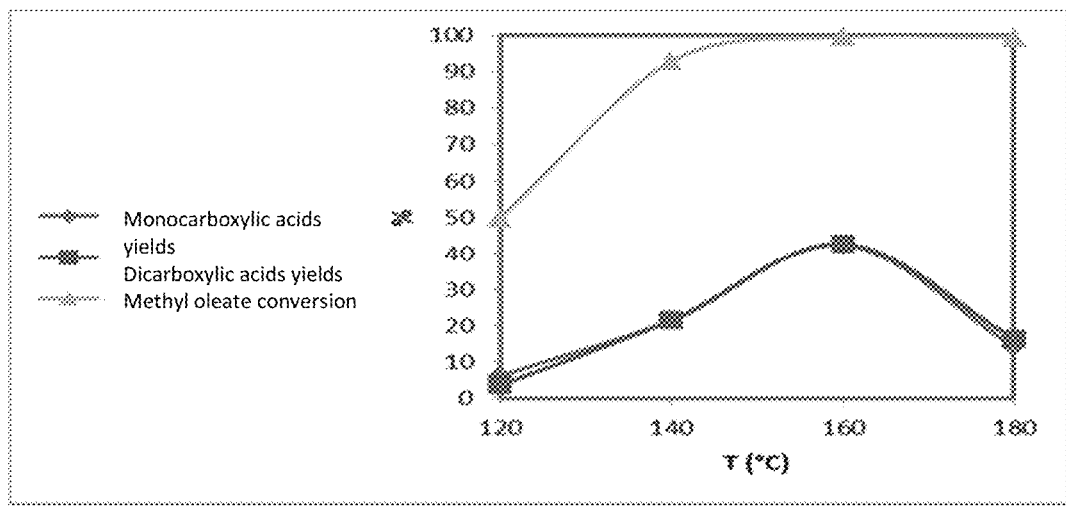

(51) Int. Cl.
    *C07C 51/25*     (2006.01)
    *C07C 67/303*     (2006.01)
    *C11C 3/00*     (2006.01)

(56) References Cited

OTHER PUBLICATIONS

Stošić, Dušan et al., "CeO2—Nb2O5 mixed oxide catalysts: Preparation, characterization and catalytic activity in fructose dehydration reaction" Catalysis Today, vol. 192, No. 1, Sep. 1, 2012, pp. 160-168.

MIXED OXIDES FOR THE OXIDATIVE CLEAVAGE OF LIPIDS USING OXYGEN TO AFFORD MONO- AND DI-CARBOXYLIC ACIDS

CROSS-REFERENCE TO RELATED APPLICATION

This application is a 35 U.S.C. § 371 National Phase Application of PCT Application No. PCT/EP2017/062616 filed May 24, 2017, which claims priority to IT Application No. 102016000053407 filed May 24, 2016. The disclosure of these prior applications are hereby incorporated by reference herein in their entirety.

This invention relates to new heterogeneous catalysts based on ternary or multiple mixed oxides comprising Cerium and Niobium and non-containing precious metals nor cobalt, that are able to produce in a single step the oxidative cleavage of unsaturated fatty acids, or their esters, or even lipids, affording mono and dicarboxylic acids.

A further object of the present invention is therefore a process for the preparation of carboxylic acids or derivatives thereof comprising the oxidation, with oxygen or oxygen containing gas, of unsaturated fatty acids or derivatives thereof in the presence of catalysts comprising mixed oxides of cerium and niobium, and optionally oxides of one or more metals selected from the group consisting of Cu, La, K, Bi.

The catalysts of the invention are particularly suitable for the oxidation of unsaturated fatty acids (FAs) having formula $R^1$—$CH_2$—[HC=CH]—$R^2$, where $R^1$ is a linear alkyl chain with 1 to 12 carbon atoms, saturated or unsaturated, $R^2$ is an alkyl group of formula —$(CH_2)_n$—COX, wherein X=—OH or —$OR^3$ ($R^3$ alkyl group) or a glyceryl group, and n may vary from 1 to 12 (only integer numbers).

The catalysts of the present invention can be used with recovered unsaturated animal or vegetal oils.

State of the Technology

The oxidation in controlled conditions of unsaturated FAs is a synthetic route useful for the synthesis of several added value chemicals. Attention is paid to derivatives of oleic acid, one of the most abundant monounsaturated FAs in nature.

The cleavage of the carbon-carbon double bond of oleic acid and similar compounds usually requires a two-step process (oxidation to diol and oxidative cleavage of the latter) while a single step oxidation is very rare, and rarely oxygen has been used as unique oxidant.

The direct cleavage has been obtained by ozonolysis or using $Re_2O_7/H_2O_2$, $H_2WO_4/H_2O_2$, $Ru(acac)_3/NaIO_4$, $RuO_2/NaOCl$, $RuCl_3/MeCO_3H$): no-one of these methods using less hazardous oxidants is enough competitive with respect to ozonolysis for an industrialization.

The two-step cleavage has been reported with potassium monopersulfate (oxone) and nickel (as in the patent application FR 2086521) or with $Re_2O_2/H_2O_2$, $RuCl_3/H_2O_2$, $NiCl_2/NaOCl$. Also in those cases oxygen was not used as oxidant.

A third route that can be found in the scientific literature is the methatetic conversion of the unsaturated FA into an acid having a terminal olefinic bond that is then oxidized (Lipid Technol. 1997, 9, 130-132).

Hydrogen peroxide ($H_2O_2$), which is largely used in the two step process (hydroxylation-cleavage), has been used as catalyst for the single step oxidation together with a tungsten based catalyst (e.g. tetrakis(oxodiperoxotungstate)phosphate), polymeric ammonium salts or cesium salts as promoters. Long reaction times and a large excess of $H_2O_2$ are nevertheless required to obtain the cleavage of the C—C double bond. Hydrogen peroxide has been used with an homogeneous catalyst based on molybdenum, ($MoO(O_2)$ $[C_5H_3N[CO_2)_2](H_2O)$), other catalysts such as $Re_2O_7$, tantalum either supported or not, or $WO_2$ and $H_2WO_4$ with very variable yield in dicarboxylic acid in the range 32-94%.

In the two step process, typically $H_2O_2$ produces the diol in presence of tungstic acid and the next step, namely the oxidative cleavage of the diol, is obtained for example using $H_2O_2$ in presence of other metal based catalysts, e.g. $Re_2O_7$ or Ru. An example of diol cleavage using oxygen has been reported by Santacesaria (Catal Today. 2003, 79/80, 59-65; Ind. Eng. Chem. Res. 2000, 39, 2766-2771) using a polyoxometalate generated from $H_2WO_4$ and $Co(OAc)_2$, where Co is the active species.

Examples of two-step cleavage industrial processes are described in WO 2008/138892 A1 and WO 2007/039481 A1.

However, in the patent and scientific literature there are few examples of heterogeneous catalysts able to use oxygen in the single pot cleavage of unsaturated fatty acids or other olefins. The heterogeneous catalysts based on cerium oxide based mixed oxides of the present invention are surprisingly able to perform such cleavage in a single step using molecular oxygen as oxidant and without requiring other catalysts, such as Cobalt or other precious metals, nor organic solvents. Noteworthy, neither $CeO_2$ nor other oxides used in the catalysts of the present invention have been reported to produce both the cleavage and the complete oxidation to carboxylic acid with molecular oxygen as unique oxidant: $CeO_2$ in stoichiometric ratio can produce aldehydes (as described in US 2012/0264956), Nb oxide (preferably together with W) have been shown to be active only with $H_2O_2$ and in the presence of a protic organic solvent (U.S. Pat. No. 5,596,111).

DESCRIPTION OF THE INVENTION

The Applicants have unexpectedly found that mixed oxides of Ce and Nb, optionally comprising oxides of one or more metals selected from the group consisting of Cu, La, K, Bi, are effective catalysts for the cleavage of double bonds of olefins such as unsaturated fatty acids or derivatives thereof and their further oxidation to carboxylic acids. Monounsaturated FAs such as oleic acid and their derivatives such as methyl oleate, lipids are the preferred starting materials. The cleavage proceeds in a simple and economic way, in solventless conditions and in moderate conditions of temperature and pressure.

Object of the present invention are therefore mixed oxides of formula $x(CeO_2)y(Nb_2O_5)$, wherein x varies from 0.2 to 10, y from 1 to 10, and the stoichiometric ratio between the cerium oxide and the niobium oxide x/y is preferably comprised between 0.2 and 10, preferably between 0.5-2 and more preferably is =1, further comprising oxides of one or more metals selected from the group consisting of Cu, La, K, Bi.

According to a preferred embodiment, the mixed oxide of the present invention have the following general formula:

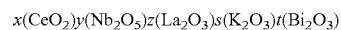

$x(CeO_2)y(Nb_2O_5)z(La_2O_3)s(K_2O_3)t(Bi_2O_3)$ where x varies from 0.2 to 10, y from 1 to 10, z from 0.1 to 5, s from 0.1 to 2 and t from 0.1 to 5.

According to a preferred aspect, x varies from 1 to 10 (preferably from 5 to 8; more preferably x=7); y varies from 1 to 10 (preferably from 5 to 8; more preferably y=7).

Preferably z varies from 1 to 5 (more preferably z=3); s varies from 1 to 2 (more preferably s=1); t varies from 1 to 5 (more preferably t=2).

According to another preferred embodiment, the mixed oxides of the present invention have the following general formula:

$$x(CeO_2)y(Nb_2O_5)m(CuO)$$

where x, y and m vary between 1and 2; preferably x=2; y=1; m=1.

The mixed oxides of the invention can be prepared according to known techniques. For example, they are advantageously prepared using the solventless technique High Energy Milling (HEM). A solid mixture containing the desired amounts of the precursor salts, oxides or carbonates of the active metal elements are milled at high speed, preferably 600-750 rpm (typically 700 rpm), by using a HEM equipment with agate baskets and balls for the necessary time (e.g. from 20 to 60 min, typically 30 min) as reported in the following examples. At the end of the milling, the resulting solids are calcined for 1 to 5 h (preferably for 3 h) at a temperature in the range 350-650° C., preferably at 550° C.

The mixed oxides described in this invention are used as catalysts for the preparation of mono- and dicarboxylic-acids or their derivatives by oxidative cleavage of unsaturated FAs or derivatives thereof.

Particularly, an object of the invention is a process for the preparation of saturated monocarboxylic and dicarboxylic acids or derivatives thereof comprising the oxidation of unsaturated carboxylic acids and/or derivatives thereof with oxygen, or a gas containing oxygen, in the presence of catalysts comprising mixed oxides of formula $$x(CeO_2)y(Nb_2O_5),$$

wherein x varies from 0.2 to 10, y from 1 to 10, the stoichiometric ratio between the cerium oxide and the niobium oxide x/y being preferably comprised between 0.2 and 10, more preferably between 0.5-2 and even more preferably being=1, optionally further comprising oxides of one or more metals selected from the group consisting of Cu, La, K, Bi.

According to a preferred aspect of the process, the catalysts comprise mixed oxides of general formula:

$$x(CeO_2)y(Nb_2O_5)z(La_2O_3)s(K_2O)t(Bi_2O_3)$$

where x varies from 0.2 to 10, y from 1 to 10, z from 0 to 5, s from 0 to 2 and t from 0 to 5.

According to a preferred aspect, z, s and t are not zero and x varies from 1 to 10 (preferably from 5 to 8; more preferably x=7); y varies from 1 to 10 (preferably from 5 to 8; more preferably y=7); z varies from 1 to 5 (preferably z=3); s varies from 1 to 2 (preferably s=1); t varies from 1 to 5 (preferably t=2).

According to another preferred embodiment, the catalysts of the present invention comprise mixed oxides of formula:

$$x(CeO_2)y(Nb_2O_5)m(CuO)$$

where x, y and m vary between 1 and 2; preferably x=2; y=1; m=1.

According to an aspect, the invention relates the oxidative cleavage process of unsaturated carboxylic acids.

Unsaturated carboxylic acids which are suitable for use in the process of the invention are monounsaturated and/or polyunsaturated carboxylic acids such as, for example, 9-tetradecenoic (myristoleic) acid, 9-hexadecenoic (palmitoleic) acid, 9-octadecenoic (oleic) acid, 12-hydroxy-9-octadece-noic (ricinoleic) acid, 9-eicosenoic (gadoleic) acid, 13-docosenoic (erucic) acid, 15-tetracosenoic (nervonic) acid, 9,12-octadecadienoic (linoleic) acid, and 9,12,15-octadecatrienoic (linolenic) acid. Monounsaturated carboxylic acids are preferred; the use of oleic acid, from the oxidative cleavage of which are mainly obtained azelaic acid and pelargonic acid, is particularly advantageous.

Mixtures of unsaturated carboxylic acids, such as for example those present in vegetable oils such as soya oil, olive oil, castor oil, sunflower oil, peanut oil, maize oil, palm oil, jatropha oil, *cuphea* oil, Carduae oils such as *Cynara cardunculus, Silybum marianum* or *Carthamus tinctorius*, Brassicaceae oils such as *Crambe abyssinica, Brassica carinata, Brassica napus* (colza), *Lesquerella*, and other oils having a high monounsaturated acids content are also advantageously used as starting materials for this process.

According to another aspect, the invention relates the oxidative cleavage process of derivatives of unsaturated carboxylic acids.

The term "derivative" refers to a carboxylic acid in which the carboxylic group is reacted so as to prevent or minimize any further reactions of this carboxylic group thus modified in the course of the process. For example, according to this invention, "derivative" of an unsaturated carboxylic acid means an unsaturated carboxylic acid in which the carboxylic acid group forms an ester bond (e.g. by reaction with an alcohol), an amide bond, a nitrile bond (e.g. by reaction with an amine), or a thioester bond (e.g. by reaction with a thiol), etc. The said derivatives may be of natural or synthetic origin. Ester derivatives are preferred.

In the case of derivatives of the ester type, the carboxylic acid group may be linked to mono-alcohols or polyalcohols. Preferred mono-alcohols comprise $C_1$-$C_9$ alkyl groups; methyl, ethyl, propyl and butyl alcohols are preferred. One example of a preferred polyalcohol is glycerol.

Methyl and ethyl esters of unsaturated carboxylic acids are particularly advantageous as starting materials for this process, in particular those obtained by the transesterification of methanol and ethanol with triglycerides present in sunflower oil having a high oleic acid content.

Mono-glycerides, diglycerides and/or triglycerides of carboxylic acids, whether synthesised or natural, are also particularly advantageous as starting materials for this process. The triglycerides present in vegetable oils or their mixtures are particularly preferred. The term "vegetable oils" refers both to the unmodified product from crushing, and to oils which have undergone chemical or physical/chemical changes, such as, for example, purification or hydrogenation treatments or enzyme enrichment processes. Examples of preferred vegetable oils are: soya oil, olive oil, castor oil, sunflower oil, peanut oil, maize oil, palm oil, jatropha oil, *cuphea* oil, Brassicaceae oils such as *Crambe abyssinica, Brassica carinata, Brassica napus* (colza), Carduae oils such as *Cynara cardunculus* (thistle), *Silybum marianum, Carthamus tinctorius, Lesquerella*, and other oils having a high monounsaturated acids content.

Unsaturated fatty acids (FAs) having formula $R^1$—$CH_2$—[HC=CH]—$R_2$ are preferred, where $R^1$ is a linear alkyl chain with 1 to 12 carbon atoms, $R^2$ is an alkyl group of formula —$(CH_2)_n$—COX, wherein X=OH or $OR^3$ ($R^3$ alkyl group) or a substituted or unsubstituted glyceryl group and n is an integer varying from 1 to 12, are particularly preferred.

According to a preferred embodiment, unsaturated fatty acids have general formula $R_1$—$CH_2$—[HC=CH]—$R_2$ where $R_1$ is a linear alkyl chain with 1 to 12 carbon atoms, preferably 6 to 9, and $R_2$ is —$(CH_2)_n$—COX moiety, where n is an integer number from 2 to 12, preferably from 6 to 8, and X is —OH, —OCH$_3$ or a glyceryl group.

The oxidizing agent of the process is molecular oxygen or a mixture comprising molecular oxygen (e.g. air or enriched air).

The process can be performed in the presence of solvents such as alcohols (e.g. methanol or ethanol), but advantageously it does not require any solvent or other additives.

The oxidative cleavage is typically carried out by adding the catalyst to the unsaturated FA or its derivative (e.g. methyl ester) or the natural lipid comprising unsaturated fatty acid, under a pressure of oxygen or air advantageously less than 50 bar. Preferably the oxygen partial pressure P2 is less than or equal to 30 bar, more preferably it is less than or equal to 25 bar and even more preferably it is between 5 and 15 bar.

The process temperatures are in a range from 80 to 180° C., preferably 100-170° C. and more preferably between 120 and 160° C. Good results were obtained at 160° C. in 3 h with a ternary equimolar oxide $(CeO_2)(Nb_2O_5)(x/y=1)$, while lower temperatures require higher reaction times (e.g. 15 h at 120° C.).

Decarboxylation is believed to occur at temperatures higher than 180° C., with consequent loss in the carboxylic acids yield.

The catalytic system of the invention advantageously avoids the use of precious metals such as Ru, Pd, Pt or Au and toxic metals such as Co or Ni.

More advantageously, the catalysts of the invention do not need dangerous oxidants such as ipochlorites, peracids or costly oxidants aggressive for plants such as hydrogen peroxide and ozone.

The catalysts hereby described allow the preparation of carboxylic acids and their derivatives preferably by a one-step oxidative cleavage process using cheap and safe oxidants such as oxygen or even air, which are non-toxic, non-corrosive and do not produce any dangerous waste. For comparison $H_2O_2$ has been used as oxidant, but it gave lower oxidative cleavage yields than $O_2$, even when it was used with molecular oxygen as co-oxidant.

According to a particular embodiment of the invention, the above described mixed oxides of Cerium and Niobium are used as catalysts for the two-step oxidative cleavage processes of preparation of carboxylic acids. Particularly, they are suitable for the oxidation with oxygen or oxygen containing gas of oxidized fatty acids (i.e. epoxidised or hydroxylated fatty acids) or derivatives thereof. The same cleavage reaction conditions as described above for the one-step process can be applied, for example. Epoxidised and hydroxylated fatty acids (i.e. diols) or their derivatives can in turn be prepared according to any of the methods known in the art, such as for example those described above.

Moreover, the catalysts work in absence of solvents (both inorganic and organic) and operate in a heterogeneous phase, are easily recoverable, for example by centrifugation or filtration of the reaction mixture.

The invention is illustrated by the following figures and examples.

FIG. 1 shows the yield of monocarboxylic acids (MCAs) and dicarboxylic acids (DCAs) in the catalytic cleavage of methyl oleate (>99%) with $O_2$ using $(Ce_2)(Nb_2O_5)$ at different temperatures. Working conditions: catalyst loading 5.5% (% w/w), $P_{O2}$=9 bar, t=3 h.

Figure 2:
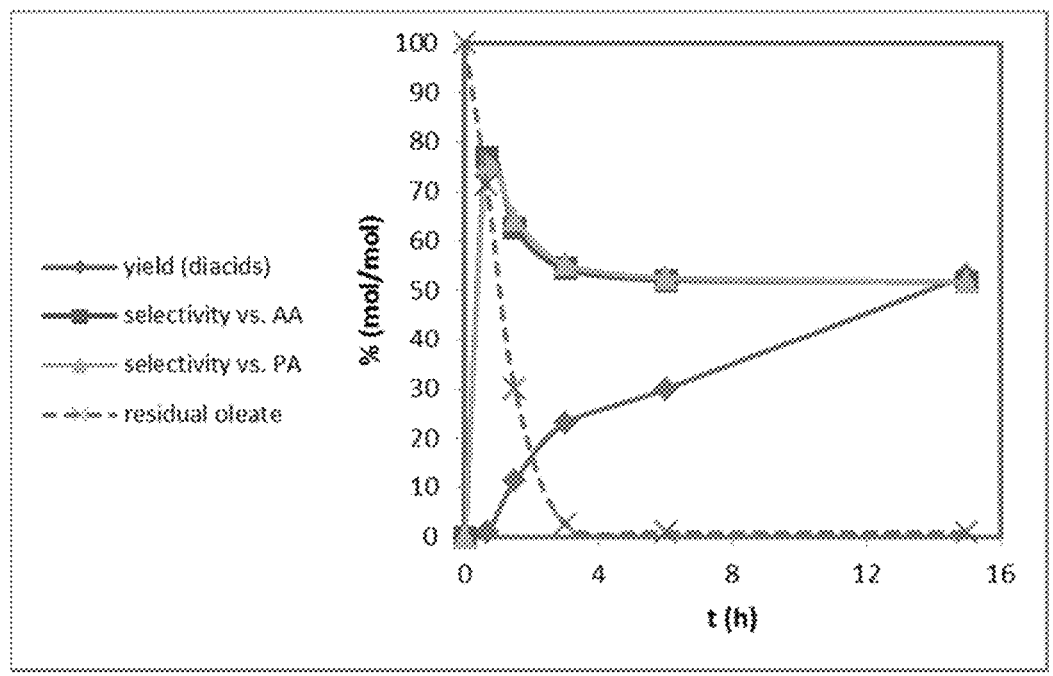

FIG. 2 shows the oxidative cleavage of methyl oleate with $7(CeO_2)$ $7(Nb_2O_5)$ $3(La_2O_3)$ $1(K_2O)$ $2(Bi_2O_3)$. The yields and selectivities towards azelaic acid (AA) and pelargonic acid (PA) are shown as function of the reaction time. Working conditions are: T=120° C., $PO_2$=9 bar, catalyst loading=5.5% (w/w).

Figure 3:
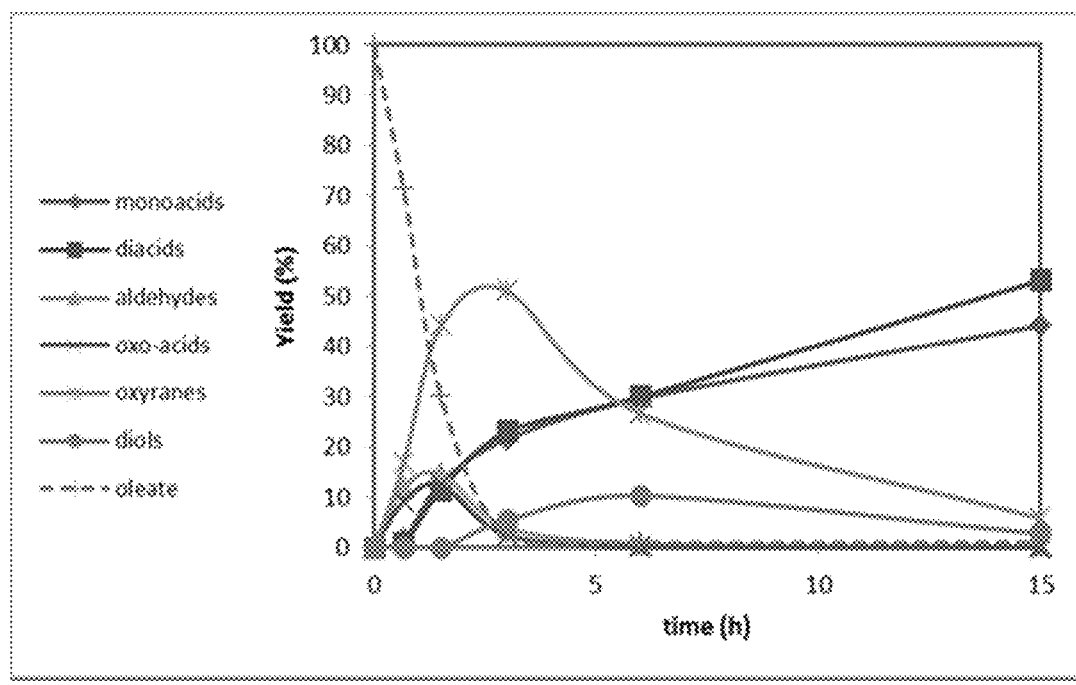

FIG. 3 shows the yield (mol/mol$_{oeate}$ %) for several products formed with time in the oxidation of methyl oleate with $7(CeO_2)$ $7(Nb_2O_5)$ $3(La_2O_3)$ $1(K_2O)$ $2(Bi_2O_3)$ with oxygen as oxidant.

EXAMPLES

The catalytic activity has been tested using methyl oleate or a low quality olive oil (a triglyceride called "lampante olive oil"). Using compressed air, at the same pressure than oxygen, the reaction is slower because oxygen is diluted by $N_2$. Higher reaction rate is achieved by increasing the air pressure.

All catalysts, prepared as described below, gave good elemental analyses and where characterized for BET, acid and basic sites.

In all cases $CeO_2$ and $Nb_2O_5$ are STREM products, $La_2O_3$, $Bi_2O_3$ and $K_2CO_3$ are purchased from Sigma-Aldrich, and CuO is a Carlo Erba product.

Example 1—Preparation of Mixed Oxides $x(CeO_2)$ $y(Nb_2O_5)$ $z(La_2O_3)$ $s(K_2O)$ $t(Bi_2O_3)$ Mixed oxides where x=7, y=7, z=3, s=1, t=2, were prepared by milling 1.204 g of $CeO_2$ with 1.860 g of $Nb_2O_5$, 0.138 g of $K_2CO_3$, 0.977 g of $La_2O_3$ and 0.931 g of $Bi_2O_3$. The final mixture after milling at 700 rpm for 30 min was calcined at 550° C. for 3 h.

Example 2—Preparation of Quaternary Mixed Oxides $x(CeO_2)y(Nb_2O_5)z(CuO)$

Quaternary mixed oxides wherein x=2, y=1, z=1 were prepared by mixing 0.564 g of $CeO_2$, 0.436 g of $Nb_2O_5$ and 0.130 g of CuO. The oxides were milled at the solid state using HEM (700 rpm for 30 min at room temperature). The final mixture was calcined at 550° C. for 3 h.

Example 3. Catalytic Oxidation of Methyl Oleate (>99%) with Ternary Mixed Oxides Using Oxygen ($P_{O2}$=9 Bar)

Ternary mixed oxides $x(CeO_2)y(Nb_2O_5)$ with x/y=0.2÷10 have been prepared from $CeO_2$ and $Nb_2O_5$. In particular, the following amounts were used 0.229 g of $CeO_2$ and 1.771 g di $Nb_2O_5$; or 0.489 g of $CeO_2$ and 1.511 g of $Nb_2O_5$; or 0.786 g of $CeO_2$ and 1.214 g of $Nb_2O_5$; or 1.128 g of $CeO_2$ and 0.871 g of $Nb_2O_5$; or 1.528 g of $CeO_2$ and 0.472 g of $Nb_2O_5$; or else 1.732 g of $CeO_2$ and 0.268 g of $Nb_2O_5$, for the desired molar ratio x. The oxides were milled at the solid state using HEM (700 rpm for 30 min at room temperature). Each final mixture was calcined at 550° C. for 3 h.

The mixed oxides catalyst (50 mg of $CeO_2$—$Nb_2O_5$) was introduced in a glass reactor with a magnetic stirrer and 1 mL of methyl oleate was added. The reactor was placed in a 75 mL autoclave, that was pressurized with $O_2$ (9 bar) and heated to T=120° C. The reaction was carried out for t=15 h. At the end the autoclave was cooled down to ambient temperature and the mixture of products recovered by centrifugation. The reaction mixture was analysed via GC after methylation using a 3% mol $H_2SO_4/CH_3OH$ mixture (60 minutes at 80° C.), extraction in hexane and filtration on anhydrous $Na_2SO_4$.

The $(CeO_2)_x(Nb_2O_5)$ catalyst, where x=1, was active in solventless conditions in the range 120-160° C. Best results were obtained at 160° C. for short (3 h) reaction time or at 120° C. for longer reaction time (15 h). In such conditions the dicarboxylic acid yield is around 40% (mainly azelaic and suberic acid) (Table 1). Other catalysts (n=mol$_{CeO2}$/mol$_{Nb2O5}$; n=0.2, 0.5, 1, 2, 5, 10) produce lower yields depending on n. Data in Table 1, were obtained working at 120° C. A similar trend is observed at 160° C. for 3 h.

TABLE 1

Oxidation of methyl oleate with $O_2$ using ternary mixed oxides. Working conditions: T = 120° C., t = 15 h; $P_{O2}$ = 9 bar; catalyst loading = 5.5% w/w.

| Product | No of C atoms | 0.2(CeO$_2$) (Nb$_2$O$_5$) | 0.5(CeO$_2$) (Nb$_2$O$_5$) | (CeO$_2$) (Nb$_2$O$_5$) | 2(CeO$_2$) (Nb$_2$O$_5$) | 5(CeO$_2$) (Nb$_2$O$_5$) | 10(CeO$_2$) (Nb$_2$O$_5$) |
|---|---|---|---|---|---|---|---|
| Dicarboxylic acids (DCAs) | total | 30.0 | 34.8 | 41.1 | 36.0 | 35.4 | 30.9 |
|  | ≤6 | 0.1 | 0.2 | 0.6 | 0.7 | 0.5 | 0.4 |
|  | 7 | 2.4 | 3.8 | 5.9 | 5.0 | 5.0 | 4.2 |
|  | 8 | 9.3 | 11.0 | 13.7 | 11.8 | 13.1 | 11.0 |
|  | 9 | 18.2 | 19.8 | 20.7 | 18.5 | 16.8 | 15.3 |
|  | 10 | 0.0 | 0.0 | 0.1 | 0.0 | 0.0 | 0.0 |
| Monocarboxylic acids (MCAs) | total | 29.1 | 34.7 | 35.7 | 31.2 | 34.8 | 30.1 |
|  | ≤6 | 1.3 | 1.6 | 1.6 | 2.0 | 1.6 | 1.3 |
|  | 7 | 3.7 | 5.3 | 5.1 | 4.6 | 5.4 | 4.9 |
|  | 8 | 8.9 | 10.9 | 9.3 | 7.8 | 9.5 | 8.3 |
|  | 9 | 15.1 | 16.6 | 19.3 | 16.4 | 17.4 | 15.3 |
|  | 10 | 0.2 | 0.3 | 0.4 | 0.4 | 0.8 | 0.2 |
| Conversion | % | 100.0 | 100.0 | 99.8 | 99.9 | 99.8 | 99.7 |
| Selectivity towards AA | AA/DCAs (%) | 60.7 | 56.8 | 50.5 | 51.4 | 47.6 | 49.5 |
| Selectivity towards PA | PA/MCAs (%) | 51.7 | 47.8 | 54.1 | 50.0 | 52.6 | 51.0 |

Example 4. Catalytic Oxidation of Methyl Oleate (>99%) with $(CeO_2)(Nb_2O_5)$ with $PO_{2=9}$ Bar at Various Temperatures The reaction system prepared as in Example 3 (ternary oxide with x/y=1) was reacted under 9 bar $O_2$ at various temperatures in the range 120-180° C. for 3 h. At the end the autoclave was cooled the catalyst separated and the liquid phase analysed as in Example 3. Data in Table 2 and FIG. 1 suggest that the temperature has a key role in the reaction and 160° C. is the best temperature. Both at 140° C. and at 180° C. the yield of PA (pelargonic acid, $C_8H_{17}COOH$) and AA (azelaic acid, HOOC—$C_7H_{14}$—COOH) are reduced.

The experiments at variable temperature show that: i) increasing the temperature increases the conversion rate of methyl oleate, ii) increasing the temperature increases the yield of dicarboxylic acids with less than 9 carbon atoms, due to decarboxylation of the products. Best compromise is represented by 3 h reaction time at 160° C. (FIG. 1) at which the conversion is complete and the yield of C9 is maximized.

TABLE 2

Yields of MCAs and DCAs in the catalytic oxidation of methyl oleate (>99%) using $(CeO_2)(Nb_2O_5)$ at various temperatures. Working conditions: catalyst loading 5.5% (w/w), $P_{O2}$ = 9 bar, t = 3 h.

| Product | No of C atoms | 120° C. | 140° C. | 160° C. | 180° C. |
|---|---|---|---|---|---|
| Dicarboxylic acids | total | 3.6 | 21.5 | 42.3 | 14.3 |
|  | ≤C6 | — | 0.2 | 3.6 | 0.1 |
|  | C7 | — | 1.9 | 9.9 | 1.7 |
|  | C8 | 0.7 | 6.6 | 11.5 | 4.1 |
|  | C9 | 2.8 | 12.8 | 17.3 | 8.5 |
|  | C10 | — | — | 0.0 | — |
| Monocarboxylic acids | total | 6.2 | 21.5 | 42.6 | 16.5 |
|  | ≤C6 | 0.1 | 1.2 | 4.9 | 1.6 |
|  | C7 | 0.6 | 2.9 | 6.7 | 3.0 |
|  | C8 | 2.2 | 6.3 | 9.8 | 5.1 |
|  | C9 | 3.3 | 9.8 | 18.2 | 6.5 |
|  | C10 | — | 0.4 | 3.2 | 0.3 |
| Conversion | % | 49.8 | 93.2 | 99.6 | 99.4 |
| Selectivity vs. AA | AA/DCAs(%) | 77.8 | 59.5 | 40.9 | 59.4 |
| Selectivity vs. PA | PA/MCAs(%) | 53.2 | 45.6 | 42.7 | 39.4 |

Example 5. Catalytic Oxidation of Methyl Oleate (>99%) with the Mixed Oxide 7(CeO$_2$) 7(Nb$_2$O$_5$) 3(La$_2$O$_3$) 1(K$_2$O) 2(Bi$_2$O$_3$) under $P_{O2}$=9 Bar In order to improve the stability of the catalyst and its activity, multiple mixed oxides were prepared. The mixed oxide 7(CeO$_2$) 7(Nb$_2$O$_5$) 3(La$_2$O$_3$) 1(K$_2$O) 2(Bi$_2$O$_3$), prepared according to Example 1, showed excellent stability in catalysis and good reaction rate and selectivity. The catalyst (50 mg) was placed in a glass reactor, kept in vacuo for 30 min to eliminate humidity and added with methyl oleate (1 mL) under $N_2$. The reactor was placed in a stainless steel autoclave that was closed, evacuated, charged with $O_2$ (9 bar) and heated to T=120° C. for a time variable between t=0.66 and 15 h. At the end the catalyst was recovered by centrifugation and the liquid processed as reported in Example 3.

Table 3 shows that MCAs and DCAs are maximized at 15 h (44.3% and 53.1%, respectively). Interestingly, the multiple catalyst is more active than the ternary one described in examples 3-4 and its composition remains unchanged at the end of the catalytic run (and EDX analysis showed the total absence of metals in the liquid phase at the end of the catalytic run). The catalyst was recovered and re-used after short calcination at 550° C. showing the same activity.

At short reaction times, the acids with Cn lower than 9 were formed in a low yield, but the conversion of methyl oleate was also low. After 45 min short chain acids were almost absent and grew with time. A time of 15 h seemed to be a good compromise between conversion and selectivity. Longer times can produce decarboxylation of the acids.

FIG. 3 and data in Table 4, give useful information about the kinetics and mechanism of conversion of the methyl oleate into the carboxylic acid. Within first 45 min, the cleavage produced oxo-derivatives that were subsequently converted into the end products. In the time interval 0.66-3 h the formation of MCAs and DCAs was observed. Me-oleate was partially converted into epoxy-derivatives (EOAs) which could afford diols and then the acids end products. After 3 h, methyl oleate was completely converted, while the formation of MCAs and DCAs continued from intermediates epoxides and diols, which concentration decreased with time. The gas phase showed the presence of $CO_2$ and $H_2$ formed by decarboxylation and dehydrogenative oxidation of cleavage products of methyl oleate.

TABLE 4

Yield (mol/mol$_{oleate}$ %) of compounds formed in the oxidation of methyl oleate with $O_2$ in presence of 7(CeO$_2$) 7(Nb$_2$O$_5$) 3(La$_2$O$_3$) (K$_2$O) 2(Bi$_2$O$_3$) (P$_{O2}$ = 9bar) with time

| Compound | Reaction time (h) | | | | | |
|---|---|---|---|---|---|---|
| | 0 | 0.66 | 1.5 | 3 | 6 | 15 |
| MCAs | — | 1.6 | 12.9 | 21.6 | 29.6 | 44.2 |
| DCA | — | 1.0 | 11.4 | 23.1 | 30.0 | 53.2 |
| Aldehydes | — | 11.8 | 14.6 | 3.9 | 0.8 | 0.3 |
| Oxo-acids | — | 9.1 | 12.4 | 2.4 | 0.2 | 0.0 |
| Oxiranes | — | 16.7 | 44.1 | 51.0 | 26.6 | 5.8 |
| Diols | — | 0.0 | 0.0 | 5.4 | 10.3 | 2.8 |
| Oleate | 99.8 | 71.3 | 30.0 | 2.7 | 1.0 | 1.0 |

Example 6. Catalytic Oxidation of Methyl Oleate with Compressed Air in Presence of 7(CeO$_2$) 7(Nb$_2$O$_5$) 3(La$_2$O$_3$) 1(K$_2$O) 2(Bi$_2$O$_3$)

The autoclave set was prepared as in Example 5 and loaded with air at 6 bar (or 40 bar) and the reaction run for 15 h at 120° C. The reaction mixture was worked up as reported in Example 3. Table 5 shows the conversion of the reagent and the yield of MCAs and DCAs with the air pressure. When the pressure of 40 bar was used, the $O_2$ pressure (8 bar) was close to that used with pure $O_2$ (9 bar). At 6 bar the conversion of oleate was not complete. A better conversion was observed at 40 bar, but it was not quantitative.

Oxiranes are present in significant amount at the end of the reaction.

TABLE 3

Yield (% in mol) in MCA and DCA in the catalytic oxidation of methyl oleate with 7(CeO$_2$) 7(Nb$_2$O$_5$) 3(La$_2$O$_3$) 1(K$_2$O) 2(Bi$_2$O$_3$) in solvent-free conditions at 120° C. as function of reaction time. Working conditions: P$_{O2}$ = 9 bar; catalyst loading = 5.5% w/w.

| Product | Alifatic chain length (No of C atoms) | Reaction times (h) | | | | |
|---|---|---|---|---|---|---|
| | | 0.66 | 1.5 | 3 | 6 | 15 |
| MCAs | total | 1.6 | 12.9 | 21.6 | 29.6 | 44.2 |
| | ≤5 | — | — | n.d. | n.d. | n.d. |
| | 6 | — | 0.4 | 0.7 | 1.1 | 2.0 |
| | 7 | — | 0.7 | 2.0 | 3.1 | 5.0 |
| | 8 | 0.4 | 3.1 | 6.1 | 8.3 | 11.4 |
| | 9 | 1.2 | 6.3 | 9.2 | 12.0 | 17.6 |
| | 10 | — | — | 0.1 | 0.2 | 0.8 |
| DCAs | total | 1.0 | 11.4 | 23.1 | 30.0 | 53.2 |
| | ≤5 | — | — | — | n.d. | n.d. |
| | 6 | 0.0 | 0.0 | 0.2 | 0.4 | 0.9 |
| | 7 | 0.0 | 0.0 | 1.8 | 3.1 | 6.8 |
| | 8 | 0.3 | 4.3 | 8.3 | 10.6 | 17.5 |
| | 9 | 1.0 | 7.1 | 12.6 | 15.6 | 27.5 |
| | 10 | 0.0 | 0.0 | 0.2 | 0.3 | 0.4 |
| Conversion of oleate | % | 28.5 | 69.8 | 97.1 | 98.8 | 98.8 |
| Selectivity vs AA | AA/DCAs(%) | 76.9 | 62.6 | 54.4 | 52.1 | 51.8 |
| Selectivity vs PA | PA/MCAs(%) | 75.0 | 64.3 | 55.4 | 52.6 | 51.8 |

TABLE 5

Catalytic cleavage of methyl oleate with compressed air at two different pressures using 7(CeO$_2$) 7(Nb$_2$O$_5$) 3(La$_2$O$_3$) 1(K$_2$O) 2(Bi$_2$O$_3$). Working conditions: T = 120° C., t = 15 h, P(air) = 6 or 40 bar, catalyst loading 5% w/w.

| Compound | Conversion/Yield at 6 bar | Conversion/Yield at 40 bar |
|---|---|---|
| C6 | 0.2 | 0.7 |
| C7 | 0.9 | 1.9 |
| C8 | 3.2 | 5.7 |
| C9 | 4.2 | 8.5 |
| C10 | 0.4 | 0.1 |
| MCAs (mol % tot) | 8.9 | 16.9 |
| Selectivity vs PA (% mol PA/mol MCAs) | 47.3 | 50.3 |
| C6 | 0.0 | 0.2 |
| C7 | 0.2 | 1.8 |
| C8 | 2.6 | 8.2 |
| C9 | 4.0 | 12.5 |
| C10 | 0.2 | 0.2 |
| DCAs (mol % tot) | 7.1 | 22.9 |
| Epoxystearates (mol %) | 42 | 22 |
| Selectivity vs Azelaic acid (% mol AA/mol DCAs) | 56.5 | 54.6 |
| Conversion (%) | 61.9 | 94.0 |

Example 7. Catalytic Cleavage of Lipids (Olive Oil) Under O$_2$ in Presence of 7(CeO$_2$) 7(Nb$_2$O$_5$) 3(La$_2$O$_3$) 1(K$_2$O) 2(Bi$_2$O$_3$)

Olive oil was used instead of methyl oleate in the oxidative cleavage. In order to have a complete conversion a higher temperature (140° C.) was used than with methyl oleate (120° C.). After 15 h at 140° C. using 9 bar of O$_2$ the total conversion of the oil was observed. The catalyst was recovered by centrifugation and the liquid phase worked up as in Example 3. The formed acids are shown in Table 6.

TABLE 6

Oxidative cleavage of olive oil with 7(CeO$_2$) 7(Nb$_2$O$_5$) 3(La$_2$O$_3$) 1(K$_2$O) 2(Bi$_2$O$_3$) under 9 bar O$_2$ at 140° C. for 15 h (MCAs = monocarboxylic acids; PA = pelargonic acid; DCAs = dicarboxylic acids; AA = azelaic acid).

| Compound (No of C atoms) | Selectivity (%) PA/MCA | Yield % MCAs | Selectivity (%) AA/DCAs | Yield % DCA |
|---|---|---|---|---|
| ≤5 | — | 38.1 | 6.9 | 43.4 |
| 6 | 5.8 | | 3.5 | |
| 7 | 16.1 | | 6.2 | |
| 8 | 11.5 | | 12.8 | |
| 9 | 21.9 | | 23.2 | |
| 10 | 2.2 | | 0.9 | |
| Tot | 57.5 | | 53.4 | |

Example 8. Catalytic Cleavage of Methyl Oleate Under O$_2$ in Presence of Quaternary Mixed Oxides 2(CeO$_2$)(Nb$_2$O$_5$)(CuO)

The catalyst prepared according to Example 2 (50 mg) was placed in a glass reactor, under Nitrogen flux, and was kept in vacuo for 30 minutes before the addition of two different substrates (Fatty Acid methyl Esters (FAMEs), 1 mL; see composition in Table 6). The mixture was left under vacuum for a further 30 minutes and then introduced into a steel autoclave which was charged with oxygen (9 bar). The mixture was allowed to react at 120° C. for 15 h. After the reaction, the autoclave was cooled in an ice bath and the resulting mixture was recovered and separated from the catalyst by centrifugation. Reaction mixtures were prepared for GC/MS analysis by direct methylation catalyzed by H2SO4. Mixture A, containing a small amount of polyunsaturated acids, was more readily oxidized than the mixture B (methyl oleate 96%; see Table 7). Indeed, although in both cases the conversion of unsaturated FAMEs was almost quantitative within 3 hours, in the case of mixture B the main part is still composed of epoxies and di-hydroxystearates which in the case of mixture A have already disappeared after 3 hours. The oxidation of Mixture A yielded 44% dicarboxylic acids after 3 hours. The DCAs yields decreased to ≈38% after 15 h, probably due to the decomposition of the alkyl chains. The oxidation of mixture B yielded only 22-23%, but most of the mixture was still composed of partial oxidation products which could be further oxidized. Therefore, mixture B requires longer reaction times.

TABLE 7

Composition (mol %) of the FAMEs starting mixtures (A: Methyl oleate, technical grade; B: methyl oleate 96%).

| Mixture | C14:0 | C16:0 | C16:1 | C18:0 | C18:1 | C18:2 | Unsaturated (%) | Monounsaturated (%) |
|---|---|---|---|---|---|---|---|---|
| A | 3.2 | 5.2 | 5.1 | 1.3 | 73.7 | 10.8 | 89.7 | 78.8 |
| B | — | — | — | 4.0 | 96.0 | — | 96.0 | 96.0 |

TABLE 8

Catalytic cleavage with O$_2$ in presence of 2(CeO$_2$)(Nb$_2$O$_5$)(CuO). Working conditions: T = 120° C., P$_{O2}$ = 9 bar, catalyst loading 5.5% (w/w).

| Mixture | t(h) | C4 | C5 | C6 | C7 | C8 | C9 | C10 | tot MCAs | C6 | C7 | C8 | C9 | C10 | tot DCAs |
|---|---|---|---|---|---|---|---|---|---|---|---|---|---|---|---|
| A | 3 | 1.1 | 2.5 | 5.8 | 5.2 | 8.0 | 11.2 | 0.8 | 34.6 | 2.6 | 3.4 | 14.9 | 17.2 | 5.9 | 44.0 |
| A | 15 | 1.3 | 2.9 | 5.9 | 5.8 | 6.9 | 10.6 | 0.6 | 34.0 | 2.2 | 3.4 | 12.5 | 16.7 | 3.5 | 38.3 |
| B | 3 | 0.3 | 0.5 | 0.9 | 3.1 | 7.8 | 9.7 | 0.3 | 22.7 | 1.0 | 2.4 | 7.6 | 10.1 | 1.3 | 22.3 |

The invention claimed is:

1. Mixed oxides of formula $x(CeO_2)$ $y(Nb_2O_5)$, wherein x varies from 0.2 to 10, y from 1 to 10, further comprising oxides of one or more metal selected from the group consisting of Cu, La, K, Bi.

2. Mixed oxides according to claim 1 of formula $x(CeO_2)$ $y(Nb_2O_5)z(La_2O_3)$ $s(K_2O)$ $t(Bi_2O_3)$ wherein z ranges from 0.1 to 5, s from 0.1 to 2, t ranges from 0.1 to 5.

3. Mixed oxides according to claim 1 which are quaternary oxides of formula $x(CeO_2)$ $y(Nb_2O_5)m(CuO)$, in which x, y, and m range from 1 to 2.

4. A process for the preparation of the mixed oxides of claim 1 by subjecting precursor salts, oxides or carbonates of the active metal elements to High Energy Milling (HME) followed by calcination.

5. Process for the preparation of saturated monocarboxylic and dicarboxylic acids or derivatives thereof comprising the oxidation of unsaturated carboxylic acids and/or derivatives thereof with oxygen, or a gas containing oxygen, in the presence of catalysts comprising mixed oxides according to claim 1.

6. Process according to claim 5, wherein the catalyst comprises mixed oxides of general formula $x(CeO_2)$ $y(Nb_2O_5)$ $z(La_2O_3)$ $s(K_2O)$ $t(Bi_2O_3)$, wherein z ranges from 0 to 5, s from 0 to 2 and t from 0 to 5.

7. Process according to claim 6, wherein x varies from 1 to 10, y varies from 1 to 10, z varies from 1 to 5, s varies from 1 to 2, t varies from 1 to 5.

8. Process according to claim 5, wherein the catalyst comprises mixed oxides of general formula $x(CeO_2)y$ $(Nb_2O_5)m(CuO)$ where x, y and m vary between 1 and 2.

9. Process according to claim 5 wherein the cleavage takes place at temperatures ranging from 80 to 180° C. in absence of solvents.

10. Process according to claim 5, wherein the unsaturated carboxylic acids are fatty acids, either vegetal or animal, of general formula $R^1$—$CH_2$—[HC=CH]—$R^2$ where $R^1$ is a linear alkyl chain with 1 to 12 carbon atoms and $R^2$ is —$(CH_2)_n$—COX moiety, where n is an integer number from 2 to 12 and X is selected from the group consisting of —OH, —$OCH_3$ or glyceryl group.

11. Process for the preparation of saturated monocarboxylic and dicarboxylic acids or derivatives thereof comprising the oxidation of unsaturated carboxylic acids and/or derivatives thereof with oxygen, or a gas containing oxygen, in the presence of catalysts comprising mixed oxides of formula $x(CeO_2)y(Nb_2O_5)$, wherein x varies from 0.2 to 10 and y from 1 to 10.

* * * * *